(12) United States Patent
Chaudhri et al.

(10) Patent No.: US 9,703,927 B2
(45) Date of Patent: Jul. 11, 2017

(54) SYSTEM AND METHOD FOR OPTIMIZING AND ROUTING HEALTH INFORMATION

(71) Applicant: Apixio, Inc., San Mateo, CA (US)

(72) Inventors: Imran N. Chaudhri, Potomac, MD (US); Shahram Shawn Dastmalchi, San Ramon, CA (US); Robert Derward Rogers, Pleasanton, CA (US); Vishnuvyas Sethumadhavan, Mountain View, CA (US); Mary Ellen Campana, San Mateo, CA (US)

(73) Assignee: APIXIO, INC., San Mateo, CA (US)

(*) Notice: Subject to any disclaimer, the term of this patent is extended or adjusted under 35 U.S.C. 154(b) by 0 days.

(21) Appl. No.: 14/162,695

(22) Filed: Jan. 23, 2014

(65) Prior Publication Data

US 2014/0200916 A1    Jul. 17, 2014

Related U.S. Application Data

(63) Continuation of application No. 13/423,159, filed on Mar. 16, 2012, now abandoned, which is a continuation-in-part of application No. 13/223,228, filed on Aug. 31, 2011.

(60) Provisional application No. 61/453,497, filed on Mar. 16, 2011, provisional application No. 61/379,228, filed on Sep. 1, 2010.

(51) Int. Cl.
| G06F 7/04 | (2006.01) |
| G06F 19/00 | (2011.01) |
| G06Q 10/06 | (2012.01) |
| G06Q 50/24 | (2012.01) |

(52) U.S. Cl.
CPC .......... *G06F 19/324* (2013.01); *G06F 19/322* (2013.01); *G06F 19/326* (2013.01); *G06F 19/328* (2013.01); *G06F 19/345* (2013.01); *G06F 19/3443* (2013.01); *G06Q 10/06* (2013.01); *G06Q 50/24* (2013.01)

(58) Field of Classification Search
CPC ...... G06Q 50/24; G06Q 10/06; G06F 19/322; G06F 19/324; G06F 19/326; G06F 19/328; G06F 19/3443; G06F 19/345; G06F 19/3487; G06F 19/3481; G06F 19/3456; G06F 19/3418
USPC .......... 726/21; 707/694, 711, 713, 726, 728, 707/730, 731, 748, 749, 750, 758, 780; 709/217, 218, 219
See application file for complete search history.

(56) References Cited

U.S. PATENT DOCUMENTS

| 7,321,861 | B1 | 1/2008 | Oon | |
| 2006/0036619 | A1 | 2/2006 | Fuerst et al. | |
| 2006/0047669 | A1 | 3/2006 | Durrence et al. | |
| 2006/0129435 | A1 | 6/2006 | Smitherman et al. | |
| 2007/0061393 | A1* | 3/2007 | Moore ................ | G06F 17/3089 709/201 |
| 2007/0106754 | A1* | 5/2007 | Moore ................ | G06F 17/3089 709/217 |
| 2007/0168461 | A1* | 7/2007 | Moore ................ | G06F 17/3089 709/217 |

(Continued)

*Primary Examiner* — Davoud Zand
(74) *Attorney, Agent, or Firm* — Kang S. Lim

(57) ABSTRACT

A method is disclosed to receive health information request (HIR), including health information request query (HIRQ) and health information request data (HIRD), and to metatag the received HIR. The metatagged HIR is reconciled based on a semantic concept and HIRS is returned.

16 Claims, 5 Drawing Sheets

(56) References Cited

U.S. PATENT DOCUMENTS

| | | | |
|---|---|---|---|
| 2008/0040151 A1* | 2/2008 | Moore | G06F 19/322 705/2 |
| 2008/0091633 A1* | 4/2008 | Rappaport et al. | 706/50 |
| 2008/0270340 A1 | 10/2008 | Abrams et al. | |
| 2009/0024615 A1* | 1/2009 | Pedro et al. | 707/5 |
| 2009/0070103 A1 | 3/2009 | Beggelman et al. | |
| 2009/0112882 A1* | 4/2009 | Maresh et al. | 707/10 |
| 2009/0136102 A1 | 5/2009 | Kimpe et al. | |
| 2009/0271221 A1 | 10/2009 | Aridi et al. | |
| 2010/0185496 A1* | 7/2010 | Hahn et al. | 705/10 |
| 2013/0291060 A1* | 10/2013 | Moore | G06F 21/6245 726/1 |

* cited by examiner

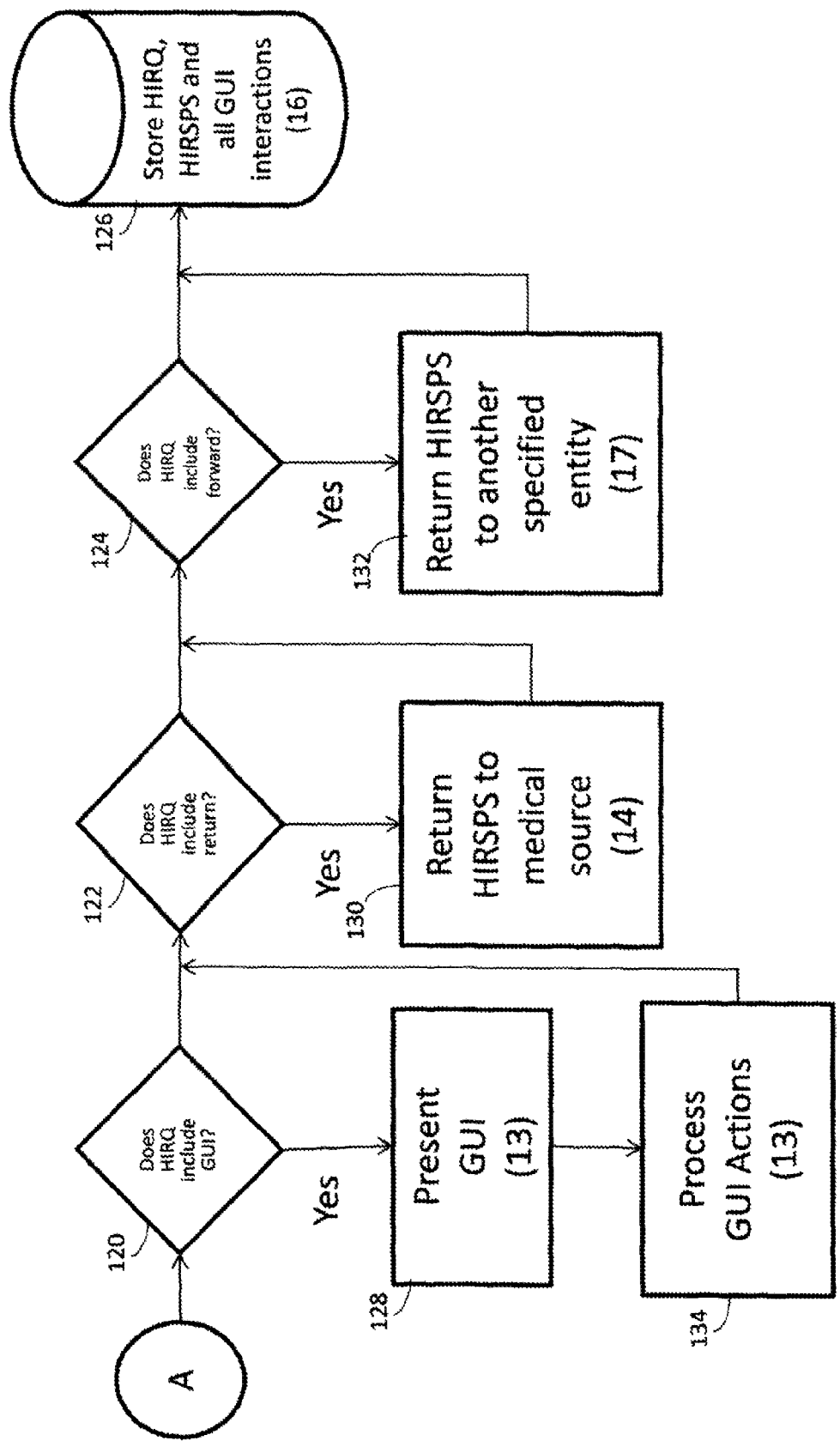

SYSTEM AND METHOD FOR OPTIMIZING AND ROUTING HEALTH INFORMATION

CROSS REFERENCE TO RELATED APPLICATIONS

This continuation application claims the benefit of U.S. Application No. 13/423,159 filed on Mar. 16, 2012, entitled "System and Method for Optimizing and Routing Health Information" which application is incorporated herein in its entirety by this reference, which application claims priority to U.S. Provisional Patent Application No. 61/453,497 by Imran Chaudhri, et al., entitled "Enhanced Medical Information Navigation Engine (MINE) System", filed on Mar. 16, 2011, and is a continuation-in-part of U.S. patent application Ser. No. 13/223,228, entitled "MEDICAL INFORMATION NAVIGATION ENGINE (MINE) SYSTEM", filed on Aug. 31, 2011, by Imran N. Chaudhri, et al., which claims priority to U.S. Provisional Patent Application No. 61/379,228, filed Sep. 1, 2010 by Ansari, et al., entitled "MEDICAL INFORMATION NAVIGATION ENGINE (MINE) SYSTEM", the contents of all of which are herein incorporated by reference as though set forth in full.

BACKGROUND OF THE INVENTION

Field of the Invention

The invention relates generally to healthcare information management and systems, and particularly to management and reconciliation of healthcare information.

Description of the Prior Art

In the field of healthcare, a problem has existed and continues to exist regarding the reliability as well as disparity of sources of information that is often critical to patient care among other reasons. The sources of information each employ a unique coding system or subset of a coding system to define concepts, diagnoses, measurements, observations, and the like. When an actor in a medical system receives new information (or "data") from an event, the question for the medical system is "Where does this data fit in?" The actor must, problematically, make an inference to determine which action to pursue.

Therefore, what is needed is a method and apparatus for reconciling healthcare information in a manner that is reliable and usable to those in the healthcare field, including patients.

SUMMARY

To overcome the limitations in the prior art described above, and to overcome other limitations that will become apparent upon reading and understanding the present specification, the present invention discloses a method and a corresponding structure for optimizing and routing health information.

Briefly, a method and system for optimizing (translating, augmenting, filtering and further optimizing) health information and routing (returning, storing and/or forwarding) it with support for wiki-based crowd-sourced quality control of information. The goals of this system are to make health information more useful and actionable for increasing revenue, care quality and patient safety, reducing costs and minimizing operational risks of organizations and individuals using health information to manage health (e.g. EHR user, systems, and patients). Information that comes into the system is routed to the organizations and/or individuals or their systems as needed after performing the optimizations required or requested.

These and other objects and advantages of the invention will no doubt become apparent to those skilled in the art after having read the following detailed description of the preferred embodiments illustrated in the several figures of the drawing.

BRIEF DESCRIPTION OF THE DRAWINGS

FIGS. 4a and 4b show a flow chart of a process for managing healthcare information, in accordance with a method of the invention.

DETAILED DESCRIPTION OF THE VARIOUS EMBODIMENTS AND METHODS OF THE INVENTION

In the following description of the embodiments, reference is made to the accompanying drawings that form a part hereof, and in which is shown by way of illustration of the specific embodiments in which the invention may be practiced. It is to be understood that other embodiments may be utilized because structural changes may be made without departing from the scope of the invention.

Figure 1:
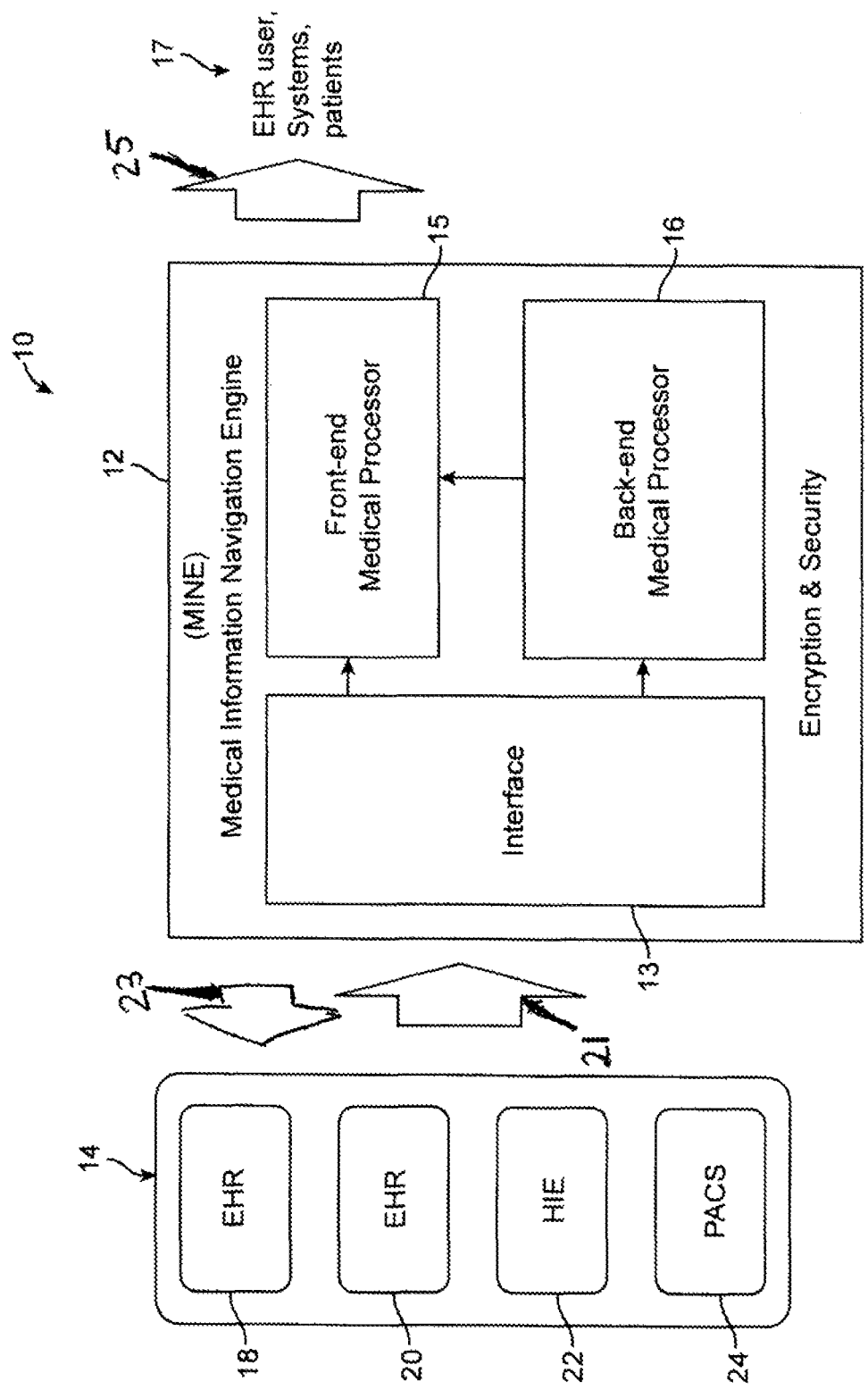
FIG. 1 shows a medical system 10, in accordance with an embodiment of the invention.

Referring now to FIG. 1, medical system 10, in accordance with an embodiment of the invention. The system 10 is shown to include medical source 14, a medical information navigation engine (MINE) 12, and medical information consumers (also referred to herein as "output" or "medical output") 17. The medical source 14 are shown to include an electronic health record (EHR) 18, EHR 20, health information exchange (HIE) 22, and a picture archiving and communication system (PACS) 24. The MINE 12 is shown to include interface 13, a back-end medical processor 16, and a front-end medical processor 15.

Healthcare information request (HIR) 21 is received from the medical source 14 by the MINE 12 and healthcare information request query (HIRQ) 23 and HIRSPS 25 is generated by the MINE 12 and sent as at least a part of the medical information that is sent to organizations and individuals (e.g. EHR user, systems, patients) 17. HIRD is comprised of any combination of coded medical data (e.g. ICD-9 code 250.00, or blood glucose measurement CPT code 82962 with measured value 103 on Jan. 1, 2010), text (for example, part of a clinical encounter note or consultation report) or image (such as a scanned colonoscopy report or lab report).

"Medical information", as used herein, refers to any health-related information, including but not limited to patient medical records, patient entered information, care team entered information, healthcare device generated information, and billing information.

The source 14 generally provides various medical information to the MINE 12. For example, the EHRs 18 and 20 each may provide information such as medical records and billing, the HIE 22 may provide information such as medical records, and the PACS 24 may provide information such as diagnostic imaging and reports.

The medical information consumers 17, which may be made of a host of entities or individuals, such as patients, clinics, medical institutions, health organization, and any other medical-related party, use information that is provided by the processor 15 of MINE 12 and that can, by way of example, consist of patients, medical systems, medical organization administrators, medical researchers, and/or EHR users. For example, user-customized processed medical information is provided by the processor 15 to a number of users within the medical information consumers 17. In this case, the processor 15 generates user-customized processed medical information to a plurality of users, with at least a portion of the user-customize processed medical information being provided to each of the users based on the relevancy of the portion being provided of each user's specific function or role and each user's associated security privileges.

The processor 16, in some embodiments, indexes identifies, maps, and consolidates medical information, received from the interface 13, and tags this information, and determines to reconcile the tagged information. In some methods and embodiments, information that is extracted from images is tagged to enhance recall of search queries. Indexing, at least in part, processes document and converts them into formats that allows for quick searching across a large collection of documents.

The information in the MINE 12 is encrypted and secure to ensure privacy of sensitive medical information.

It is understood that the sources 14 of FIG. 1 includes merely some examples of the sources that communicate with the MINE 12 and that other sources, known to those in the field, are contemplated. Similarly, the output 17 may be used by those or entities not discussed herein but that are contemplated and within the scope and spirit of the invention.

The interface 13 serves to receive information that is in various forms, such as but not limited to text, html, CCD, CCR, HL7 and any other type or format of information. The interface 13 then provides to the processors 15 and 16 information, as needed.

The processor 16 receives some of the medical information that the interface 13 processes and performs certain tasks to process it, such as indexing, semantic meta-tagging, and reconciliation. Indexing takes processed documents and converts them into formats that make it easy to quickly search across a large collection of documents. Semantic meta-tagging embeds information into the medical information that is relevant thereto and that can be later used to search for certain information for the purpose of reconciliation and search, among many others.

One aspect of consolidation, reconciliation and de-duplication, generally refers to removing of redundant patient medical records, such as, multiple records for the same individual appearing as though the records are for different individuals or multiple data elements that are recorded similarly but slightly differently in the different sources. In this case, the processor 16 recognizes that the records belong to a single individual or are the same data and just recorded differently and automatically consolidates them. The patient or a user of the system 10 may also manually perform reconciliation. The processor 16 advantageously determines whether or not reconciliation is performed.

The processor 16 outputs the indexed, tagged and reconciled information to the processor 15. The foregoing tasks are a generalization and further details of each are provided below.

The processor 15 performs certain tasks on the information provided by the interface 13 and the processor 16, which include query, search, presentation, and quality checking. The output of the processor 15 is the output of the MINE 12, or output 17.

The MINE 12, through the processor 15, in some embodiments and methods, invites members of a medical care team to join it thereby allowing distributed user-organized care teams.

Querying, as performed by the processor 15, is the ability to receive, as input, a free text query, from a user, (i.e., a query without any restrictions on the structure)—and converting the free text query into commands to a medical search engine, such as Medical Lexical Search Engine and the MATRIX (Medical Application Terminology Relationship IndeX) Concept Search Engine, using a sophisticated query processing engine optimized to work with medical queries. The results of the search engine are sent to the presentation display planner—which decides the most relevant presentation given the user's organization and role (e.g. the provider, search query program, a healthcare administrator, a study administrator, and the patient). The presentation discussed below, receives such information. In some embodiments and methods, the medical information or user information is processed to suggest relevant queries.

Search, as performed by the processor 15, is built around the concept of Zero-Click Relevance—or the ability to get to all the relevant information an actor in the healthcare system requires by typing in just a single query. The search engine, within the processor 15, performing the search comprises an indexing and searching, as will become apparent shortly. Optionally, search results may be securely embedded into third party programs. In some embodiments, searching involves determining presenting (also referred to herein as "providing") access to specific relevant data based on a search query, the patient, and the user's specific function and/or role and security privileges. A user may be within the output 17 and security privileges are either determined by the MINE 12 or by the patient or both. The information that is uploaded to the MINE 12 by users, such as in output 14 (in some embodiments) is searched by the processor 15. The uploaded information may include information such as but not limited to status posts, records, and images. Such user-uploaded information is routed automatically to the output 17, as needed.

Some aspects of the search are now discussed relevant to an example. Assuming, by way of example, that Dr. Smith, an internal medicine physician, sees a new patient, Joan Sample, who presents with a complaint of chest pain. Joan has brought several continuity-of-care documents (CCDs) and a 600-page pdf file representing of her medical chart. She has seen a cardiologist who uses NextGen's electronic medical record (EMR) and a gastroenterologist who uses eMD's EMR and she has recently visited a local emergency room. Dr. Smith uses the search of the various methods and embodiments of the invention to efficiently assemble the relevant information he needs. Dr. Smith selects Joan Sample as the patient and enters the clinical context "chest pain" in the search bar of a screen presented by the MINE 12 (examples of such screens are shown in subsequent figures herein). He is presented with relevant lab results, such as CKMB, troponin, and amylase; relevant diagnostic results, such as prior electrocardiograms (EKGs) and the most recent chest computed tomography (CT) scan; and all progress notes and consult reports in which concepts relevant to chest pain, like "GERD" and "cardiac stress test", are mentioned. Two distinct types of searches are combined, in accordance with a method and embodiment of the invention, to retrieve information medically relevant to Joan's complaint: 1) Lexical search, where text in the patient record is searched for occurrences of the search term, its variants and synonyms; and 2) Medical concept search, where data that is medically related to the search term is retrieved. Medical concept search finds relevant structured data with standardized codes, such as lab results, and text results, such as progress notes, which include terms medically related to the search term. In Joan's case, a search for "chest pain" returns a CKMB lab result and a reference to the most recent chest CT scan. Accordingly and advantageously, the Lexical and Medical concept search solves Dr. Smiths' information overload problem by returning information in the chart most relevant to determining the etiology of Joan's chest pain complaint. Further, in some embodiments, the presentation, discussed shortly, presents a united view of Joan's history by reconciling and de-duplicating data from multiple sources that may be coded and described differently. Redundant data is automatically reconciled even if it is described differently by differently sources.

Presentation, as performed by the processor 15, is displaying health information to the requesting user in a way that reduces the number of clicks and maximizes the amount of meaningful information delivered based on the interpreting the intent of the user query.

Quality checking, as performed by the processor 15, is checking of the quality of medical information provided by various sources, i.e. source 14, by the patients, structured data, and unstructured data, in a Wiki-like mannered setting whereby the users can help maintain and improve the quality of information displayed. The foregoing tasks, performed by the processor 15, are further described in detail below. Additionally, the users or patients may make comments regarding medical information, in a Wiki-like manner.

In summary, the MINE 12 transacts medical information including the interface 13 receiving medical information from a number of medical sources (such as within the source 14) for processing, identifying, mapping, and consolidating by the medical processor 16, providing access to specific relevant data, based on a user's security privileges, within the identified, mapped, and consolidated medical information, based on user-specific functions or roles, performed by the processor 15, and generating user-customized processed medical information to a number of users, such as within the output 17, with at least a portion of the user-customized processed medical information being provided to each of the users based on its relevancy to each user's specific function or role and each user's associated security privileges.

Figure 2:
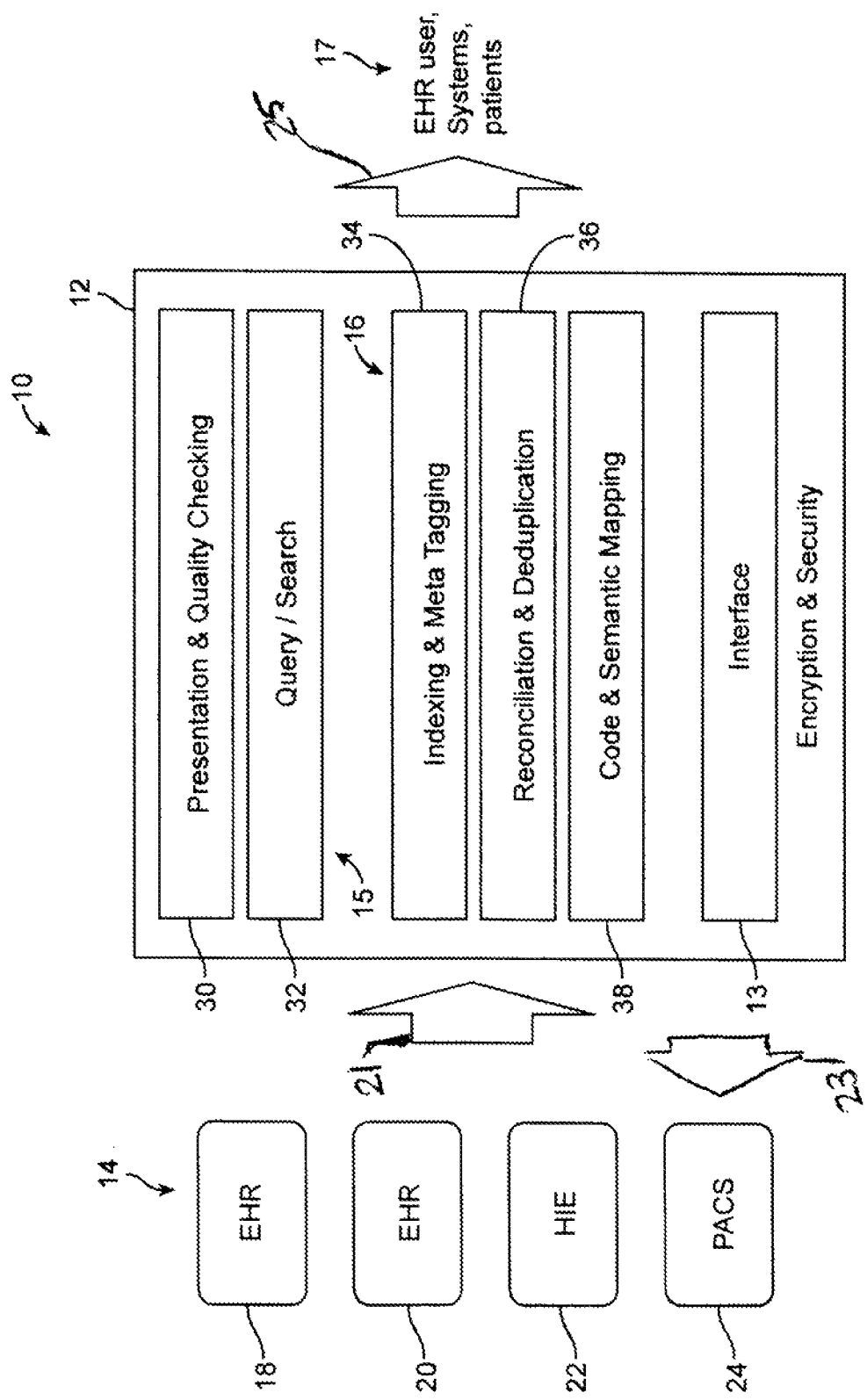
FIG. 2 shows further details of the MINE 12 of FIG. 1, in accordance with an embodiment of the invention.

FIG. 2 shows further details of the system 10, particularly the MINE 12 thereof. That is, the processor 16 is shown to include an indexing and metal tagging module 34, which includes an indexing module and a meta tagging module (both of which are not shown in FIG. 2 in the interest of clarity), which may be a module, as shown in FIG. 2 or two physically separate modules. The processor 16 is further shown to include a reconciliation and de-duplication module 36, which also can be broken out into two modules, a reconciliation module and a de-duplication module, and a code and semantic mapping module 38, which also may be a single module or multiple modules. The modules 34, 36, and 38 communicate with one another.

The processor 15, in some embodiments, includes display and visualization 40 executing on one or more servers 38, which may be any suitable computing engine, similar to the servers 32, including but not limited to PCs or servers. The display 40 is used to construct presentation and display information to users, such as the patient's records, billing information, and other types of medical information. The display 40, in some embodiments, also performs processing of some of the functions of the processor 15.

The foregoing modules may be software programs, executed by a computer or computing engine of suitable sorts, or may be implemented in hardware.

Figure 3:
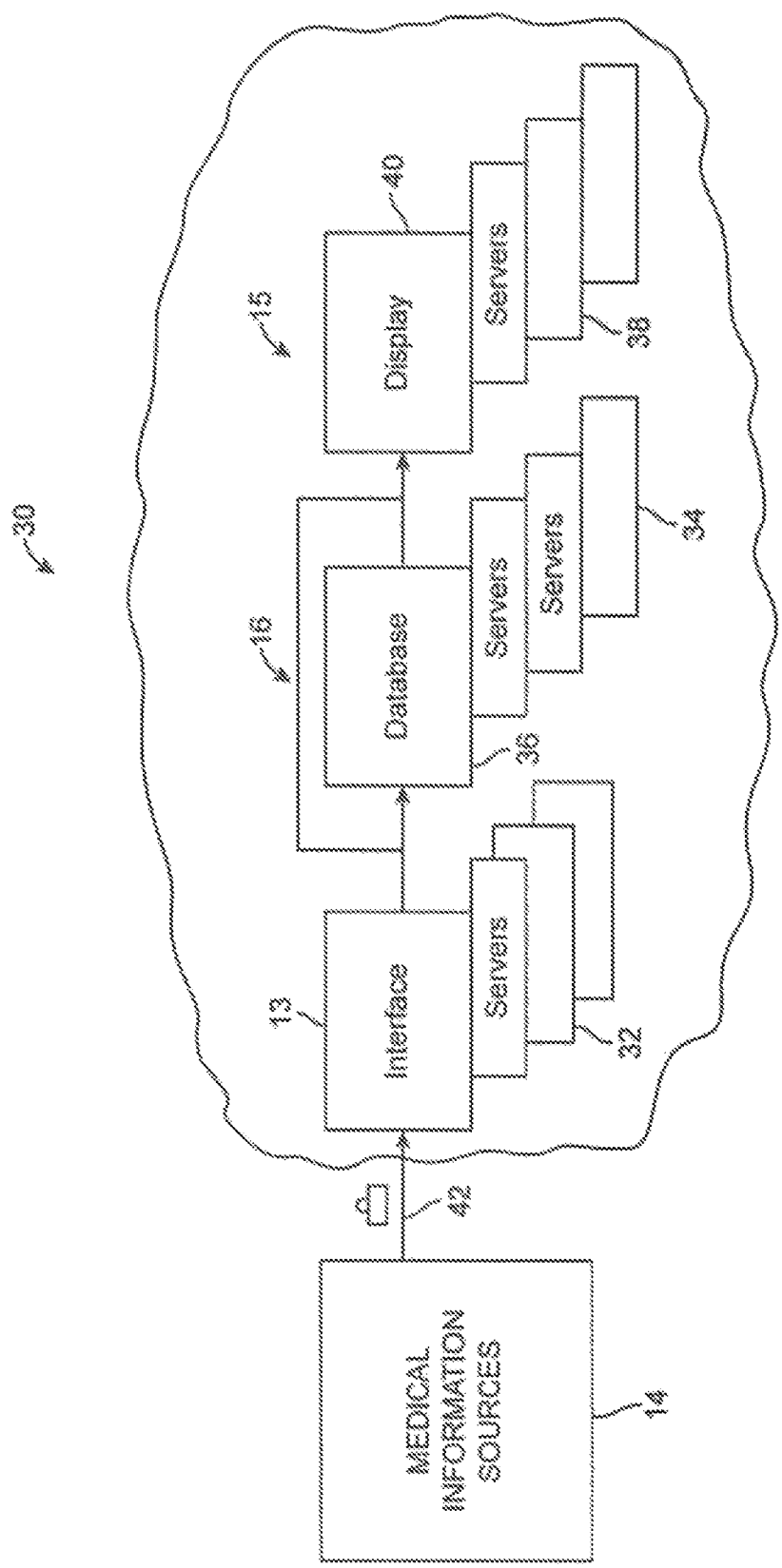
FIG. 3 shows an exemplary embodiment implementing the system 10 using various devices.

FIG. 3 shows an exemplary embodiment implementing the system 10 using various devices. That is, the medical system 30 is analogous to the system 10 and is shown to include the sources 14 coupled to communicate, securely, through the secure communication link 42, to the interface 13. The link 42 may be any suitable communication channel allowing information, of various formats and types, to be transferred to the interface 13 in a secure and encrypted fashion. Exemplary communication channels of which the link 42 is made include the Internet, VPN connections over the Internet, private dedicated digital lines such as T1, T3, E1, E3, SONET, and other fiber optic formats.

The interface 13, in some embodiments, is a software program that executes on one or more servers 32, which can be a server of any kind of suitable computing engine, such as personal computer (PC). The servers 32 receive secure information through the link 42 from the sources 14. The processor 16, in some embodiments, includes the module 36 and one or more servers 34, which may be any suitable computing engine, similar to the servers 32, including but not limited to PCs or servers.

The module 36 and servers 34 perform the tasks discussed above relative to the processor 16 and the display 40 and servers 38 perform the tasks discussed above relative to the processor 15 though these processors may and often perform additional tasks related to medical information, some examples of which are presented and discussed below and the rest of which are contemplated and achieve the various advantages, results and functions presented herein.

The processor 15, in some embodiments, includes display and visualization 40 executing on one or more servers 38, which may be any suitable computing engine, similar to the servers 32, including but not limited to PCs or servers. The display 40 is used to construct presentation and display information to users, such as the patient's records, billing information, and other types of medical information. The display 40, in some embodiments, also performs processing of some of the functions of the processor 15.

As shown in FIG. 3, the servers 32 are coupled to the module 36 and the servers 34, and to the display 40 and the servers 38 and the module 36 and servers 34 are coupled to the display 40 and the servers 38.

In some embodiments, the interface 13, servers 32, module 36, servers 34, display 40, and servers 38 are remotely located relative to the sources 14 and in some embodiments, remotely located relative to one another. Further, they are considered a part of the Internet cloud where, performing their tasks in a manner known as "cloud-computing". However, other manner of achieving the functions and advantages of the invention, including various other of implementation, not shown in FIG. 3 or other figures herein and/or not discussed are contemplated.

Figure 4A:
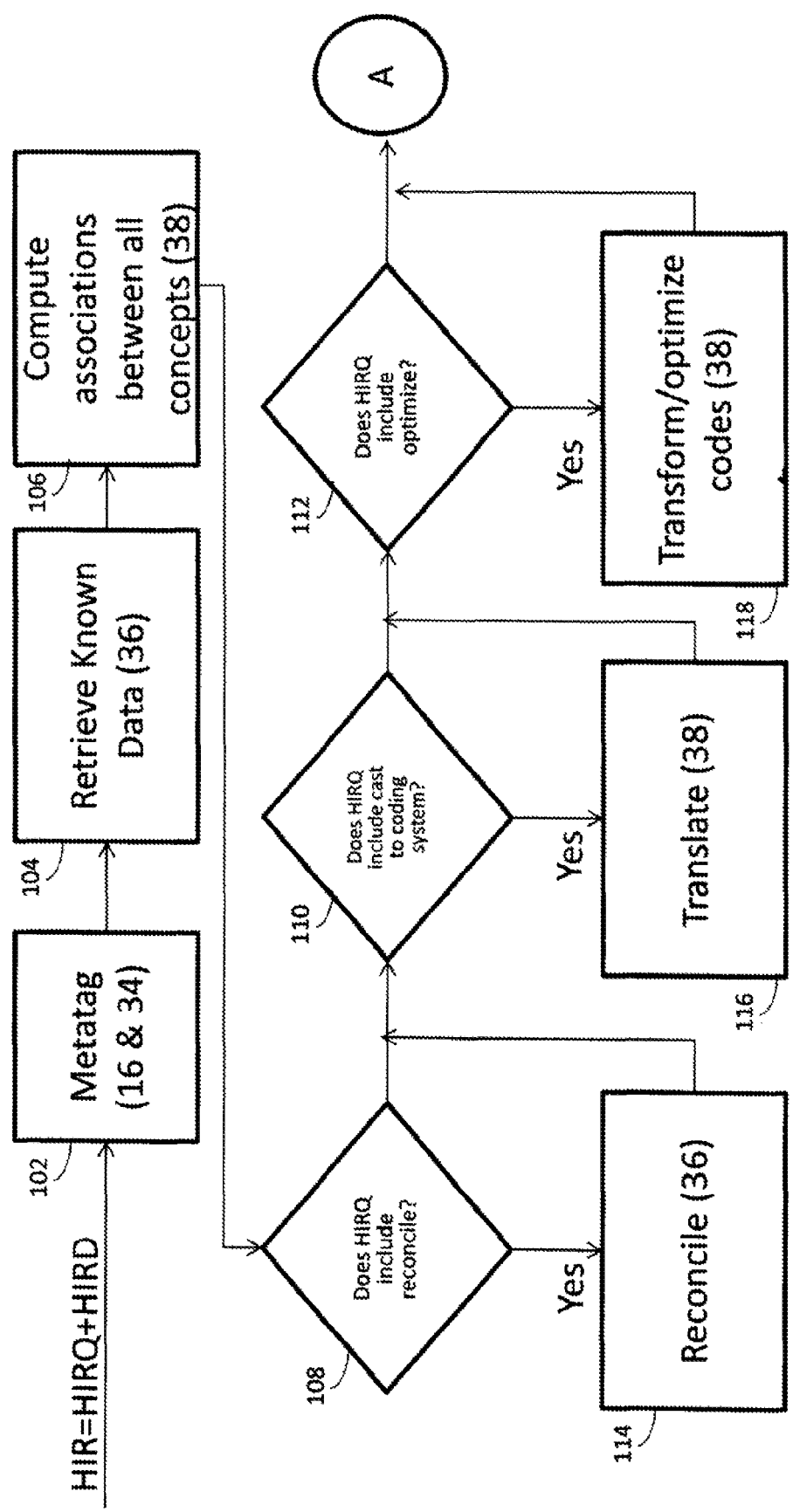

FIGS. 4a and 4b show a flow chart of a process for managing healthcare information, in accordance with a method of the invention. The steps of FIGS. 4a and 4b can be executed by a computer processor or device as a software program and the like. For example, using the embodiment of FIG. 1, the processors and other structures, such as databases and servers, may be employed to carry out the steps and process of FIGS. 4a and 4b.

In FIG. 4a, at step 102, the HIR is received and metatagged by the processor 16 and module 34 of the MINE 12. The metatag step 102 adds descriptive information to the HIRD of HIR and interprets the data of the HIRD in a manner that is suitably precise and processes the data by medical analytics (metatagging), readily known to those in the art, and subsequently generates a metatagged HIR (also referred to herein as "HIR1 ") for use in the next step 104. The HIR1 includes extracted concepts and annotations.

In particular, in step 102, text is first extracted from the received HIR from, for example, images using optical character recognition (OCR) technology. Then natural language processing is used to identify all healthcare concepts that are described in any text found in the HIRD. The universe of possible concepts currently includes all known medical terminologies (as documented, for instance in the NCBO Bioportal) along with all concepts and terms that are found in the healthcare data available to the system. As new concepts and terms are identified in incoming text, they are added to the universe of concepts. For each piece of text that is related to a concept, all possible associations are added. Multiple levels of association can be annotated via a hierarchical structure, which can be represented in a number of ways including XML. The text is further processed to determine what type of document or document section the text represents, what measurements, dates and other context pertain to the concept and whether the concept is stated in the negative (for example, "no history of diabetes" would yield the negated concept "diabetes", while "diabetes is controlled" would yield a positive instance of the concept "diabetes."

Execution of the step 102, in some embodiments and processes, causes more than 65% of key clinical data to be represented by textual data (including that from images), which is not accessible to computerized analytical systems. In order to create an optimal representation of any healthcare information (for example, for the purpose of augmenting a patient's problem list, medications list and allergies with other known information about the patient, reconciling these lists into a single set of non-redundant items and then casting these items into the representation or coding system most advantageous to the user) it is necessary to include this textual information. The inclusion of such textual data in the translation, augmentation and filtering of healthcare data is unique to this system.

Next, at step 104, known data is retrieved. That is, the HIR1, generated by the step 102, is utilized to retrieve from a system search document, such as the system search document 203 of the U.S. patent application Ser. No. 13/223,228, filed on Aug. 31, 2011, by Imran Chaudhri, et al. and U.S. Provisional Patent Application No. 61/582,213, filed on Dec. 30, 2011, by Imran N. Chaudhri, et al., all data related to the contents of the HIR1, and generates HIR2 for use at step 106. The HIR2 includes the HIR1 with all retrieved data appended thereto.

Further, at step 104 additional information is retrieved from one of the structures of the MINE 12 that is necessary to fulfill the request contained in HIR1. The contents of the HIRQ are organized into a query and submitted to the Query/Search 32 of the MINE 12, to retrieve all data (both structured, textual and image) that matches the criteria defined in HIRQ. For example, if the request contained in HIR1 is to be used for a reconciled medication list for a patient identified by the ID 12345, a query for all medications relevant to patient ID 12345 (including those for other patient IDs that have been identified as synonymous with patient ID 12345 ) will be issued to the MINE 12. The resulting medication data, which includes text and images that have been annotated (see step 102 for a specific annotation process) are returned to step 104 and are appended to the HIR1, resulting in the HIR2, which is subsequently passed on to step 106.

At step 106, the HIR2 is used to compute associations between all concepts. "Concepts" are medical concepts such as medications, allergies, problems and diagnoses, procedures, immunizations, measurements, observations, symptoms and the like.

As described hereinabove, because of the importance of textual data in healthcare documentation, it is critical to include both structured data and annotated textual data during the process of reconciling, augmenting, disambiguating, and/or filtering of healthcare data. The inclusion of such textual data in the translation, augmentation and filtering of healthcare data is unique to this system.

More particularly, at step 106, computing associations between all known concepts is performed by using the HIR2 request from the 104 step, assembling all data items from the data portion of HIR2 into pairs, assigning a degree of association measure between each element in the pair, and then outputting HIR3, which includes the HIR2 with the resulting additional pairings and association measures appended to it, to be used as input in step 108.

At step 106, the MINE 12 retrieves association measures for pairs of concepts from the MATRIX, discussed in U.S. patent application Ser. No. 13/223,228, and U.S. Provisional Application No. 61/582,213 referenced hereinabove. An association measure is a number between 0 and 100 that represents how medically related the two concepts are: a 0 means there is no relationship between the two concepts, and a 100 means they are synonymous (also known as "variants"). Each resulting pair plus association measure is appended to the HIR2 object. When all pairs have been considered and their associations appended to the HIR2 object, the resulting object HIR3 is passed to step 108.

Before translating, augmenting and filtering data contained in HIR, at step 106 it is necessary to associate semantic concepts with it, so that data can then be reconciled and disambiguated. Also, because in healthcare, closely related but different concepts may be used by different actors to describe the same observation, patient or finding, it is necessary to have continuous measures of association that can be used in a fuzzy match, rather than exact match, strategy (as will be described below relative to step 114).

In accordance with the foregoing, advantageously, medically relevant measure of association between two healthcare concepts is assigned.

Referring still to FIG. 4a, after the step 106, a determination is made at 108 as to whether or not the HIRQ is reconciled. If it is determined that HIRQ has been reconciled, the process executes step 114 and if not, the process continues to 110. During step 114, HIR3 is processed by using the HIR2 from the step 106, recursively organizing all data items into groups based on fuzzy matching of the semantic concepts represented by the data and further organizes the items within each group according to properties defined in the HIRQ query part of HIR3. In this manner, HIR4 is generated and includes the HIR3 annotated with the resulting organizational structure from the reconciliation process, to be used at 110.

During, the step 114, the data in HIR3 is grouped according to the type of reconciliation requested in the HIRQ portion of the HIR3 request. Specifically, the request can include a set of explicit rules for fuzzy matching of the data items or can reference default rules at step 114. Rules define how strongly components of each data item must be associated in order to consider them related enough to be grouped or reconciled. For example, if HIR3 includes a request to create a reconciled list of all medications included in HIR3, and further specifies that all medications of the same formulation be grouped together regardless of manufacturer, prescription instructions and prescription date, then an exact match on the formulation of each medication would be required for inclusion in each reconciled medication group. As each new member of a group is added, the prototypical group member is re-evaluated. This prototypical group member is useful for computational efficiency in some analytical processes, can be used in some display applications and can be returned as the single representative of the group in some applications. Further grouping and organization within the group can then be carried out. For example, exact duplicates of data items from different sources are combined into new subgroups.

At step 114, if HIR3 requests that different instances of grouped concepts be considered as separate groups, further grouping might be carried out. For example, the same medication prescribed on separate occasions could either be placed in a single group or distinct groups, depending on whether HIR3 requests that different instances of the same semantic concept be separated or combined.

Another example of HIR3 relates to a fuzzy match being requested to create a reconciled problem list for a specific patient, where the data elements of HIR3 include "pneumonia" and "viral pneumonia" concepts. The association measure between these two concepts will be high (i.e. close to, but less than, 100). If HIR3 requests an exact match, then the resulting problem list will include both "pneumonia" and "viral pneumonia". If HIR3 requests a close fuzzy match then a single concept for the group (including both "pneumonia" and "viral pneumonia") will be returned. Once all groupings have been completed, the data is in a form to be organized and all elements at this level are organized according to the HIR3 request. For the medication example, all distinct prescriptions for a particular medication formulation can be organized according to time order, prescriber, manufacturer, medication type (e.g. statin, analgesic, antibiotic, etc) or other attribute, as specified in the incoming HIR3 request.

At 108, the determine as to whether reconciliation is performed or not applies to the HIR before it is used at the determination 110. The decision to reconcile in step 108 may be based on an explicit request to reconcile the data, or it may be implied. Implied actions can be identified using algorithms that may range from a look-up to computational inference via artificial intelligence to advanced machine learning. These algorithms may also be combined serially or in parallel. An implied request to reconcile could be, for example, if HIR includes a request to generate a problem list that is compliant with a specific standards-based format. It may be implicit in that format that reconciliation be performed to remove redundant items from the problem list, in which case the system could infer that the reconciliation step should be performed.

At 110, a determination is done as to whether translation is needed or not and if so, the process continues to step 116, otherwise, the process continues to 112. At the step 116, translation of the HIR is performed before the process continues to 112. The decision to translate at 110 may be based on an explicit request to translate the data, or it may be implied. Implied actions can be identified using algorithms that may range from simple look-up to computational inference via artificial intelligence to advanced machine learning. These algorithms may also be combined serially or in parallel.

An implied request to translate could be, for example, if HIR includes a request to generate a problem list that is compliant with a specific standards based format. It may be implicit in that format that a certain coding system be used (such as ICD-9 or SNOMED CT), in which case the system could infer that the translation step should be performed to ensure compliance with the desired output format.

More particularly, at step 116, the process at step 116 is initiated when the HIRQ includes an explicit request to translate or implies a request to translate. The step 116 converts medical concepts that are represented using one coding system to equivalent or similar concepts in another coding system. Conceptually, it is like converting words in English to words in another language like Spanish. By 'coding system' we mean a systematic categorization or ontology of concepts including but not limited to the standardized categorization schemes that are widely used in various medical information sources and consumers of medical information, for example: ICD-9, ICD-10, HCC, CPT, SNOMED CD, RXNORM, UMLS, Loinks.

The step 116 is significant because the medical information industry has evolved to have many coding systems for representing medical concepts for different purposes (e.g. billing, case management, prescriptions, epidemiology, quality reporting). Medical Information Sources 14 and consumers of medical information 17 or processes therein often depend on receiving information in a specific coding system. For instance, a quality reporting subsystem within an EHR may require ICD9 codes and be unable to process information that is represented in UMLS. The step 116 is necessary to achieve the goal of using all of the available medical information, not just that information that happens to already be in the appropriate coding system.

The step 116 is advantageously an automatic, software-driven process. In current practice converting information represented in one coding system to another is typically driven by human knowledge and experience. For example, medical billing systems require concepts to be represented in certain coding systems (e.g. ICD9, CPT). However, CMS requires Medicare Advantage claims to be submitted in a specialized coding system, HCC. To receive payment for caring for these patients, providers must convert the billing information that is supported by their Medical Information Sources (e.g. EHR, practice management systems) from the typical coding systems (e.g. ICD9, CPT) to the HCC coding system. Providers accomplish this by hiring trained human coders to assign HCC codes based on their own knowledge and experience and the available data for each patient.

Also, at step 116, the translation process is encapsulated as a process that is separate from the Medical Information Sources themselves. While some Medical Information Sources and Medical Information consumers may have some capabilities for converting between certain coding systems, MINE 12 provides comprehensive ability to translate between all major coding systems. It is accurately applied in a consistent way for all incoming data, regardless of the source.

Further, step 116 is situated within a larger system, MINE 12, which has access to many records for the patient that the HIRD applies to. This information could be used to resolve ambiguities. By ambiguity we mean when one code in the source coding system could be converted to multiple codes in another coding system, but the resulting codes in the new coding system are not equivalent to each other and may even conflict. By resolving ambiguities we mean selecting only the most appropriate code(s) given all of the information that is known about the patient.

Additionally, step 116 occurs within a larger system, MINE 12, which has access to many records for many patients. This information could be used to identify associations between medical concepts in various coding systems and improve accuracy of translation using machine learning techniques.

Further, at step 116, significant savings in the cost of developing, maintaining and accurately applying coding systems is experienced. In the medical industry the various coding systems are often in competition for widespread use. There is no single gatekeeper for these coding systems. They are updated on different timelines and in different ways. All of this means that maintaining and applying accurate and up-to-date information about all of the various systems is time-consuming, error-prone and costly for the individual source 14 or medical information consumer. Moreover, there is a duplication of effort as each Medical Information Source or medical information consumer must create essentially the same code. By consolidating at the step 116, and separating it from the individual health information sources and health information consumers we reduce all of these costs for those entities.

Further, at step 116, a consistent conversion for each set of codes to each other is realized regardless of the source 14 it can lead to improved consistency of an individual's health record across different Medical Information Sources 14. It can also reduce variability for comparisons across different Medical Information Sources 14, for instance in the kind of comparisons done by quality reporting systems.

Also, at step 116, a large data set is accessible and this step can be accurately and appropriately perform than a hypothetical module that performed the same function but did not have access to information beyond the HIRD. Example are: ambiguity resolution from above, identifying new associations and improving accuracy through machine learning from above.

At step 116, data is received that will eventually be included in the Health Information Response (HIRSPS). This could be a metatagged version of the original Health Information Request Data (HIRD), which is contained in the Health Information Request (HIR). Alternatively, it could be a reconciled data set that combines the HIRD and other known data as described in outputs of Reconcile 114. Another input is the desired coding system, which is contained in the Health Information Request Query (HIRQ), which is part of the Health Information Request (HIR). Another input to Translate 116 is the larger set of known data. The output of step 116 is the data that will eventually be included in the Health Information Response (HIRSPS), represented in the coding system that was specified in the HIRQ.

The step 116 converts concepts from one coding system to another using algorithms that may range from simple look-up to computational inference via artificial intelligence to advanced machine learning. The specific algorithms used may be customized for different source coding system and desired coding system pairs. They may also be combined serially or in parallel. The algorithms may or may not make use of published crosswalks, findings in the medical literature, or knowledge that has been learned from aggregated data. They may operate over just the data that is to be translated or consider the data that is to be translated in conjunction with additional known data about the patient.

It is noted that after the step 114, the process of FIG. 4*a* continues to 110 and after the step 116, the process continues to 112.

At 112, the determination is made as to whether or not to transform/optimize codes or not and if so, transforming/optimizing is performed at step 118 on the HIR before it is passed on to and used at the determination at 120 of the FIG. 4*b*. The decision of step 112 may be based on an explicit request to transform or optimize the data, or it may be implied. Implied actions can be identified using algorithms that may range from look-up to computational inference via artificial intelligence to advanced machine learning. These algorithms may also be combined serially or in parallel.

An implied request to transform or optimize the data could be, for example, if HIR includes a request to generate a problem list that is optimized for Medicare Advantage HCC coding. It is implicit in HCC coding that some representations for semantically identical (or nearly identical) concepts are preferred over other representations. For example, ICD-9 code 427.89 (Other specified cardiac dysrhythmias) would have significantly lower value to a health system than the closely related ICD-9 code 427.81 (Sinoatrial node dysfunction). In this case is both codes could be used to represent data in HIR, then the system can infer that the transform/optimize process of step 118 should be performed to ensure optimal value of the data to the application that consumes the output data object.

At step 118, transformation and optimization is initiated when the HIRQ includes an explicit request to transform/optimize or implies a request to transform/optimize. It is noted that an implied request to translate is anticipated, for instance, if the request contains an instruction to forward to a particular quality measurement system and the outcome is known to be better than the outcome will be better if the code set for that purpose is optimized before forwarding it.

During step 118, further, information that is represented in a particular coding system can be translated or transformed to a subset of that coding system that is likely to result in improved outcomes for a downstream process or set of downstream processes in the health care industry. "Coding" refers to the translation step 116. "Downstream" process refers to workflow function that must be performed by one or many medical information sources or consumers of health care information (e.g. submitting claims to insurance companies, reporting quality measures, detecting adverse events involving medication conflicts and/or allergies).

For example, the medical condition 'diabetes mellitus' may be represented using more than 50 individual codes within the ICD9 coding system. Even for a case of diabetes that is newly diagnosed or poorly understood there are at least 6 potential codes: 250, 250.0, 250.00, 250.01, 250.02 and 250.03. For providers who care for Medicare Advantage patients, some of these codes result in payment increases to adjust for the additional cost of treatment for the condition (e.g. 250.0, 250.00). Other codes do not (e.g. 250). The step 118 would in this case convert incoming 250 ICD9 codes to 250.01 and/or 250.03 ICD9 codes, which are more likely to result in improved outcomes, in this case payments to providers, for a downstream process, in this case Medicare Advantage Risk Adjustment. This steps allows all relevant information to be useful for downstream process, despite the inherent noise introduced by the variety of available coding systems and processes of translating between them (e.g. step 116), human-driven translations, translations within Medical Information Sources). This inherent noise results from underlying conceptual discrepancies due to the fact that in the medical industry the various coding systems do not match up exactly in terms of individual concepts. This inherent noise also results from the fact that different goals require different levels of detail. For example one reason you might be dealing with this is you might have information that was entered in for the purposes of clinical decision-making, like a note or a problem in an EHR, which was then converted to ICD9. If the original coding system did not include the distinction between type1 or type2 then at the point of conversion to ICD9 there would be no way to unambiguously map it to a single ICD9 zcode or even a set of codes that would be appropriate for all downstream processes. A decision would need to be made during the conversion: exclude the information, use codes for both Type I and Type II diabetes, use the general category, or pick one Type. All of these possibilities would result in noise in the form of lost information and/or potential errors depending on how the information would later be used. Once the conversion was made, it would be difficult to roll back.

Using diabetes mellitus as an example, for the purposes of the downstream process of Clinical Decision Support it is very important to know whether a specific case is type I or type II. For the purposes of Medicare Advantage Risk Adjustment, however, either type results in the same payment. Thus, for the downstream process of Clinical Decision Support, converting ICD9 250 (category: diabetes mellitus) to 250.00 (diabetes mellitus without mention of complication, type II or unspecified type, uncontrolled) or 250.03 (diabetes mellitus without mention of complication, type I [juvenile type], uncontrolled) without detailed knowledge about which one is more accurate and/or confirmation by a clinician might be disadvantageous and/or dangerous. On the other hand, converting 250 to 250.00 or 250.03 might be reasonable and appropriate for the downstream process of Medicare Advantage Risk Adjustment.

Current processes often ignore the possibility that these types of noise may have been introduced in prior steps. They instead assume that the code is equivalent to the concept and operate on it as such (resulting in advantages a1 and a2 and a3 below).

There are some special-purpose systems that do this sort of processing for a particular outcome (e.g. billing optimization). The differences between our design and those are 1) we have access to more additional information for the individual patient, (resulting in advantage b1 below) 2) we have access to additional information aggregated across many patients (resulting in advantage b2 below), 3) we optimize for multiple outcomes (resulting in advantage b3 below), 4) we are separate from the Medical Information Source and provide consistent outputs regardless of the Medical Information Source (resulting in advantage b4 below). The resulting HIRSPS of this step will be maximally useful for a specified downstream process. Additionally:

A1) All relevant information is used, regardless of noise that may have been introduced due to concept mismatches and/or differences in level of detail needed for different purposes. (compared to potential approaches that exclude codes that are not an exact match)

A2) Reduced potential for errors to be introduced in the interest of including more information (compared to potential approaches that operate at the most general level to identify more related concepts)

B1) improved accuracy of conversion in the case of a specific patient or set of patients (e.g. looking at medications to infer which type of diabetes is being treated), B2) Improved accuracy of inferences for anyone, even when we do not have additional medical information for an individual patient (e.g. knowledge of which type of diabetes is more prevalent, knowledge of which types of medications are associated with each type of diabetes)

B3) Able to compensate for specific biases in data that are introduced due to concept mismatches and level-of-detail issues (e.g. knowledge that 250 is used when the type of diabetes (I or II) is irrelevant to the task at hand, not truly unknown, suggests that if the information is relevant for the current optimization we should seek additional details within the patient's medical information which may be represented in a different coding system (e.g. medication list).

B4) Savings (see equivalent advantage in the step 116)

B5) Consistency for comparison across Medical Information Sources, for instance for applying quality measures (strategic example, see equivalent advantage in Translate, 116)

B6) Consistency when multi-sourced data is aggregated for the purposes of optimizing a downstream process (e.g. reducing noise in order to detect a small signal, as in our work with Stanford where the goal is to predict adverse events as new drugs come to market). This also applies to step 116.

One input to the step 118 is the data that will eventually be included in the Health Information Response (HIRSPS). This could be a metatagged version of the original Health Information Request Data (HIRD), which is contained in the Health Information Request (HIRD). Alternatively, it could be a reconciled data set that combines the HIRD and other known data as described in outputs of the step 114. This data may be in the original coding system(s) or it may be in another coding system as described in the outputs of the step 116.

Another input is an indicator of the downstream process that the output should be optimized for (e.g. Clinical Decision Support, Medicare Advantage Risk Adjustment, Quality Reporting), which is contained in the Health Information Request Query (HIRQ), which is part of the Health Information Request (HIR). Another input to the step 118 is the larger set of known data.

The output of the step 118 is the data that will eventually be included in the Health Information Response (HIRSPS), represented in the specific codes that have been optimized for the downstream process that was specified in the HIRQ.

At step 118, concepts are converted and represented in a coding system that is all-inclusive to a subset of that coding system that is optimized for a particular downstream process. This conversion process uses algorithms that may range from look-up to computational inference via artificial intelligence to advanced machine learning. The specific algorithms used may be customized for different downstream processes and for different coding systems. They may also be combined serially or in parallel. The algorithms may or may not make use of published crosswalks, findings in the medical literature, or knowledge that has been learned from aggregated data, including models of translation processes. They may explore the impact of multiple possible outcomes on the downstream process before producing an outcome. Additionally, they may operate over just the data that is to be transformed/optimized or consider the data that is to be transformed/optimized in conjunction with additional known data about the patient. An example of 'exploring the impact of multiple possible outcomes' would be sending different version of the same information represented in different possible code sets to Pophealth, a publicly, government-supported, reference implementation for quality measurement, and identifying the best set via gradient descent or some other machine learning algorithm for optimization.

After 112, the process continues to 120 where a determination is made as to whether or not graphical user interface (GUI) shall be applied to the HIR at step 128 or not before 122. If this decision is positive, the process continues to step 128, otherwise, it continues to 122. The decision to move onto step 128 may be based on an explicit request to present the GUI for wiki-based quality control, user confirmation or other modification by the user, or it may be implied. Implied actions can be identified using algorithms that may range from simple look-up to computational inference via artificial intelligence to advanced machine learning. These algorithms may also be combined serially or in parallel.

At step 128, information is displayed by the Presentation and Quality Checking of the MINE 12, in a way that it can be understood and acted on by a person via graphical user interface (GUI) elements that are known in the art (e.g. formatted text, tables, forms, checkboxes, drag and drop interfaces, drop-down lists). The information thus displayed may include the HIRD that is contained in the HIR and/or outputs of any/all prior steps 102, 104, 106, 114, 116 and 118.

Step 128 offers user involvement in that medical sources 14 and/or consumers of medical information may have a need or desire for human involvement at certain steps in the process (e.g. diagnosis code changes may need to be certified by clinicians for legal reasons) and this is enabled, at least partially, by the step 128. Human involvement may be necessary to achieve quality, especially when there is uncertainty, missing information, or gaps in the conceptual information. An example is that a system may not yet have a suitable model of when it is appropriate to convert ICD9 250 to ICD9 250.00 or 250.03 at step 118. In this situation, at the step 128, the original code and the suggested conversion is displayed and allowing it to later be confirmed or rejected in by the step 134. This will immediately result in the most appropriate coding decision according to the human user (i.e. a data quality improvement). It may also contribute to improving the model at step 118 by operating on future HIRQs.

At the step 128, the overall process provides support for wiki-based crowdsourcing of quality control. "Wiki-based crowdsourcing", as used herein, allows multiple trusted users to act on the information (e.g. modify, add, delete, augment, filter) before it is transmitted and/or stored. Changes and authors of those changes are logged to allow for customization (e.g. a one of the medical information sources of the source 14 may accept actions of certain users and reject actions of others) and roll-back (e.g. going back to the original coding system). In contrast, the prior art process for quality control in the Health Industry is for new documents to be created during each visit. These documents contain a snapshot of what a particular provider described as the true state of a patient. The process of constructing this snapshot usually involves some review of information from previous visits (e.g. paper chart review, template population in an EHR). All information, true or erroneous, that is added during a visit remains in the patient's record from that time forward. Mechanisms for one doctor to document comments on or opinions about information contained in a prior chart is typically limited free text comments in a new snapshot, which may or may not be found or connected with the original information for future encounters. There is no support for ongoing discussions about treatment within the patient's health information documents, though it may occur via other channels (e.g. telephone, email, face-to-face conversations between members of the care team).

Accordingly, quality is improved—errors are removed and MINE 12 converges on just that information that stakeholders (members of the care team, etc.) feel is current, accurate and relevant. Further, efficiency is improved by connecting the dots only needs to happen once, not every time a doctor reviews a chart.

At step 128, data to be displayed (original HIRQ and output from previous process in the diagram) is received and processed, as discussed herein. This data includes flags indicating what to display (optionally output in previous steps in the diagram) and instructions about how it should be displayed (original HIRQ and output from previous process in the diagram) . . . (how=what kind of action needs to be supported and the information the user will need to carry out that action . . . e.g. simple confirmation may just be a message, while drag and drop needs individual elements and how they have been categorized. Input contains both.)

The outcome of the step 128 is a representation that is visible to a user and supports actions/GUI interactions on elements of that representation e.g. click, drag, select, enter text, submit.

Exemplary GUI at step 128 is implemented using GUI elements known in the art and listed above. One implementation is described U.S. patent application Ser. No. 13/223,228 as "DisplayMerge".

After the step 128, the process continues to step 134 where actions are interpreted by users within a GUI such that the sources 14 and consumers of medical information can use them. For example, if a person performs the action of clicking a checkbox next to a particular code within a GUI presented at step 128, the processed GUI actions at step 134 may allow or prevent the code from being included in the Health Information Response (HIRSPS), the final output of the MINE 12, on the basis of whether the result of the action was checking or unchecking the box.

Medical sources and consumers of medical information may have a need or desire for human involvement at certain steps in the process (e.g. diagnosis code changes may need to be certified by clinicians for legal reasons). Human involvement may be necessary to achieve quality, especially when there is uncertainty, missing information, or gaps in the conceptual information. Example: the system may not yet have a good model of when it is appropriate to convert ICD9 250 to ICD9 250.00 or 250.03 at the step 118. In this situation, at step 128, the original code and the suggested conversion are displayed so that it can later be confirmed or rejected at step 134. This will immediately result in the most appropriate coding decision according to the human user (i.e. a data quality improvement). It may also contribute to improving the model for the step 118 operating on future HIRQs.

Including process GUI actions at step 134 at this point in the overall process of FIGS. 4a and 4b provides support for wiki-based crowdsourcing of quality control. "Wiki-based crowdsourcing" allows multiple trusted users to act on the information (e.g. modify, add, delete, augment, filter) before it is transmitted and/or stored. Changes and authors of those changes are logged to allow for customization (e.g. a Medical Information Source may accept actions of certain users and reject actions of others) and roll-back (e.g. going back to the original coding system). In contrast, the current process for quality control in the health industry is for new documents to be created during each visit. These documents contain a snapshot of what a particular provider described as the true state of a patient. The process of constructing this snapshot usually involves some review of information from previous visits (e.g. paper chart review, template population in an EHR). All information, true or erroneous, that is added during a visit remains in the patient's record from that time forward. Mechanisms for one doctor to document comments on or opinions about information contained in a prior chart is typically limited free text comments in a new snapshot, which may or may not be found or connected with the original information for future encounters. There is no support for ongoing discussions about treatment within the patient's health information documents, though it may occur via other channels (e.g. telephone, email, face-to-face conversations between members of the care team). Accordingly, in this system quality is improved—errors get removed, system converges on just that information that stakeholders (members of the care team, etc.) feel is current, accurate and relevant and efficiency is improved—connecting the dots only needs to happen once, not every time a doctor reviews a chart.

The outcome of step 134 is the final HIRSPS, in which information that may have been reconciled, translated and/or transformed/optimized may also have been filtered, modified, augmented, added, deleted, or commented via GUI interactions by one or more users.

Exemplary implementations of step 134 include using GUI elements known in the art and listed above or alternatively, the "DisplayMerge" referred to herein. It is noted that in alternative methods, multiple actions can not be performed and the actions cannot result in changes to the display, which can then be operated on.

After step 134, the process continues to 122 and after the step 130, the process continues to 124.

At 124, a determination is made as to whether or not to return the HIRSPS to Another Specified Entity at step 132. "Another Specified Entity" is an entity such as one included in the source 14. If the result of this determination is positive, the process continues to the step 132, otherwise, the process continues to 126. The decision to return HIRSPS to the outputs 17, at 124, may be based on an explicit request to return an output data object to the outputs 17, or it may be implied. Implied actions can be identified using algorithms that may range from look-up to computational inference via artificial intelligence to advanced machine learning. These algorithms may also be combined serially or in parallel.

At 122, it is determined whether or not the Health Information Response (HIRSPS) should be routed ("returned") to the source 14. The HIRSPS contains the HIRD after it has been optimized (translated, augmented, filtered and further optimized). The decision to return HIRSPS to the source 14, at 122, may be based on an explicit request to return an output data object to the medical source 14, or it may be implied. Implied actions can be identified using algorithms that may range from simple look-up to computational inference via artificial intelligence to advanced machine learning. These algorithms may also be combined serially or in parallel.

At step 130, the HIRSPS is returned and the complete request from step 120 or step 134 (depending upon the specific flow), is used to assemble a data object according to the instructions contained in HIRQ and the original HIR is returned and the newly created data object is provided to the medical source 14.

The HIRQ portion of the incoming request includes a specification for the data to be returned to the medical source 14. Previous steps in the process carried out translation, augmentation, filtering, transformation, optimization and reconciliation of the data according to this specification. In step 130, the resulting data is assembled into a data object according to the specification in HIRQ. This data object can be represented in any number of formats, including but not limited to JSON, XML, standards-based formats such as CCD, CCR and CDA, and other proprietary formats. The transport mechanism can be web services, IHE protocols, secure file transfer, proprietary API or any other means to transport a data object.

At step 134, The return HIRSPS to Another Specified Entity of step 132 takes as input the complete request from step 120 or 134 (depending upon the specific flow), assembles a data object according to the instructions contained in HIRQ and returns the original HIR and the newly created data object to the outputs 17. The outputs 17, herein, in an exemplary process herein, is another specified entity and not MINE 12.

The HIRQ portion of the incoming request includes a specification for the data to be forwarded to another specified entity (outputs 17. Previous steps in the process carried out translation, augmentation, filtering, transformation, optimization and reconciliation of the data according to this specification. In step 132, the resulting data is assembled into a data object according to the specification in HIRQ. This data object may or may not contain all of the data and query contents of the original HIR object. For example, it may be required to send a reconciled list of current problems as computed by the system to a third party, without explicitly including the original data contained in HIR. The data object output to 17 can be represented in any number of formats, including but not limited to JSON, XML, standards-based formats such as CCD, CCR and CDA, and other proprietary formats. The transport mechanism can be web services, IHE protocols, secure file transfer, proprietary API or any other means to transport a data object.

At 126, the store HIRQ, HIRSPS and all GUI interactions of step 126 use, as input, the output from the step 124, and store it for future use by the MINE 12. The specific items stored are the HIRSPS object and the GUI interactions from step 134 (if any). HIRSPS includes the original query HIRQ along with the data component HIRD modified by any of the translation, augmentation, filtering and reconciliation system steps that were performed in the process. Depending upon the specifications of HIRQ, these can include metatagged information, such as done at step 102, or retrieved known data as done at step 106, and concepts as done at step 106, or reconciled information, as done at step 114, translated information as done at step 116, transformed/optimized codes as done at step 118, and/or processed GUI actions, as done at step 134. The GUI interactions are a complete record of all interactions between the user and the GUI. The importance of this information is that it is possible to apply the same set of translation, transformation, filtering and augmentation steps that were done by the user in the GUI to data in a subsequent request. Additionally, this information is important for quality control, logging and algorithm improvement purposes.

The actual format and method of storage can include, but is not limited to, serialized data objects, files, relational database, noSQL or other key-value store or any other method that is capable of storing and retrieving this data when needed by the system.

Accordingly, according to one of the processes of FIGS. 4a and 4b medical information, such as HIR, including health information request query (HIRQ) and health information request data (HIRD), is received and metatagged. The metatagged HIR is reconciled based on a semantic concept and HIRS is returned. An example is a patient with pneumonia where multiple occurrences of this condition are noted/coded in various places and in various forms. These occurrences are found by MINE 12 from the storage 203 based on the HIRQ or rules and methods about what is to be reconciled and what is desired (problem list).

Although the invention has been described in terms of specific embodiments, it is anticipated that alterations and modifications thereof will no doubt become apparent to those skilled in the art. It is therefore intended that the following claims be interpreted as covering all such alterations and modification as fall within the true spirit and scope of the invention.

What is claimed is:

1. In a medical information navigation engine (MINE), a computerized method of transacting health information comprising:
   receiving a health information request (HIR) from a user;
   retrieving and meta-tagging health information in response to the HIR using a medical information navigation engine (MINE) wherein meta-tagging the health information includes:
      identifying and tagging medical concepts associated with the meta-tagged health information, wherein the tagging medical concepts includes identifying associations between HIR data and medical concepts, wherein the medical concepts are standardized codes and text data medically related to a search term;
      appending the identified medical concepts to the health information of the HIR;
      identifying all additional medical concepts associated with the health information of the HIR as new information is added to the health information of the HIR to generate multiple levels of associated medical concepts;
      determining associations between medical concepts by assembling every element of the health information into pairs with all other elements of the health information, and assigning a degree of association measured between each element of the pair;
      annotating associations between multiple levels of associated medical concepts in a hierarchical structure;
      processing the HIR to determine whether each of the medical concepts in the health information of the HIR is positive or negated based upon reference;
      wherein the medical concepts include medications, allergies, problems and diagnoses, procedures, immunizations, measurements, observations and symptoms;
   creating multi-dimensional relationships between the medical concepts using the MINE, wherein the multi-dimensional relationships indicate relevancy of apixions along dimensions of the multi-dimensional relationships; and wherein the meta-tagged health information is reconciled by mapping based on at least one semantic concept; and
   providing relevant health information based on the multi-dimensional relationships to the user.

2. The computerized method of claim 1 wherein the reconciliation includes at least one lexical search, and wherein at least one textual patient record is searched for occurrence of search term, its variants and synonyms, and the reconciliation further includes at least one concept search wherein data that is medically related to the search term is retrieved.

3. The computerized method of claim 1 further comprising consolidating and de-duplicating data, thereby removing redundant medical information.

4. The computerized method of claim 1 wherein the reconciliation includes using a set of explicit rules for fuzzy matching of the data items or referencing default rules.

5. The computerized method of claim 1 wherein the reconciliation includes recursively organizing data items into groups based on fuzzy matching of the semantic concepts represented by the data and further organizes the items within each group according to properties defined in the query.

6. The computerized method of claim 1 further comprising augmenting, disambiguating and filtering of health information, and wherein the health information includes documentation such as structured data and annotated textual data.

7. The computerized method of claim 6 further comprising translating the health information, and wherein the translating, augmenting and filtering of the health information includes support for wiki-base crown-source quality control of information thereby enabling the health information to be more actionable by increasing revenue, quality of care and patient safety, and reducing cost.

8. The computerized method of claim 1 further comprising transforming of the health information, and wherein the transformation includes converting concepts from one coding system.

9. A medical information navigation engine (MINE) configured to transact health information, the MINE comprising:
   a processor completing the steps of:
      meta-tag health information in response to a health information request (HIR) from a user, wherein the meta-tagging of the health information includes identifying and tagging medical concepts associated with the meta-tagged health information, wherein the tagging medical concepts includes identifying associations between HIR data and medical concepts, wherein the medical concepts are standardized codes and text data medically related to a search term;
      append the identified medical concepts to the health information of the HIR;
      identify all additional medical concepts associated with the health information of the HIR as new information is added to the health information of the HIR to generate multiple levels of associated medical concepts;
      determine associations between medical concepts by assembling every element of the health information into pairs with all other elements of the health information, and assigning a degree of association measured between each element of the pair;
      annotate associations between multiple levels of associated medical concepts in a hierarchical structure; and
      process the HIR to determine whether each of the medical concepts in the health information of the HIR is positive or negated based upon reference, wherein the medical concepts include medications, allergies, problems and diagnoses, procedures, immunizations, measurements, observations and symptoms;
   a mapper configured to create multi-dimensional relationships between the medical concepts, wherein the multi-dimensional relationships indicate relevancy of apixions along dimensions of the multi-dimensional relationships, and wherein the meta-tagged health information is reconciled by mapping based on at least one semantic concept; and a visualizer configured to provide relevant health information based on the multi-dimensional relationships to the user.

10. The MINE of claim 9 wherein the reconciliation includes at least one lexical search, and wherein at least one textual patient record is searched for occurrence of search term, its variants and synonyms, and the reconciliation further includes at least one concept search wherein data that is medically related to the search term is retrieved.

11. The MINE of claim 9 wherein the processor further consolidates and de-duplicates data, thereby removing redundant medical information.

12. The MINE of claim 9 wherein the reconciliation includes using a set of explicit rules for fuzzy matching of the data items or referencing default rules.

13. The MINE of claim 9 wherein the reconciliation includes recursively organizing data items into groups based on fuzzy matching of the semantic concepts represented by the data and further organizes the items within each group according to properties defined in the query.

14. The MINE of claim 9 wherein the processor further augments, disambiguates and filters health information, and wherein the health information includes documentation such as structured data and annotated textual data.

15. The MINE of claim 14 wherein the processor further translates the health information, and wherein the translation, augmentation and filtration of the health information includes support for wiki-base crown-source quality control of information thereby enabling the health information to be more actionable by increasing revenue, quality of care and patient safety, and reducing cost.

16. The MINE of claim 9 wherein the processor further transforms the health information, and wherein the transformation includes converting concepts from one coding system.

* * * * *